United States Patent
Elyakov et al.

(10) Patent No.: US 6,384,084 B2
(45) Date of Patent: May 7, 2002

(54) HISTOCHROME AND ITS THERAPEUTIC USE IN OPHTHALMOLOGY

(75) Inventors: Georgy Borisovich Elyakov; Oleg Borisovich Maximov; Natalya Petrovna Mischenko; Evgenia Alexandrovna Koltsova; Sergei Alexandrovich Fedoreev; Ljutsia Ignatievna Glebko; Natalya Petrovna Krasovskaya; Alexandr Alexeevich Artjukov, all of Vladivostok (RU)

(73) Assignee: Tikhookeansky Institut Bioorganicheskoi Khimii Dalnevostochnogo Otdeleniya Rossiiskoi Akademii Nauk, Vladivostok (RU)

( * ) Notice: Subject to any disclaimer, the term of this patent is extended or adjusted under 35 U.S.C. 154(b) by 0 days.

(21) Appl. No.: 09/832,789

(22) Filed: Apr. 12, 2001

Related U.S. Application Data

(63) Continuation of application No. PCT/RU99/00248, filed on Jul. 21, 1999.

(30) Foreign Application Priority Data

Oct. 12, 1998 (RU) .......................................... 98118370

(51) Int. Cl.$^7$ .............................................. A62K 31/05
(52) U.S. Cl. ....................................... 514/731; 514/912
(58) Field of Search .................................. 514/731, 912

(56) References Cited

U.S. PATENT DOCUMENTS 5,985,937 A  11/1999  Bonal de Falgas et al. . 514/737

FOREIGN PATENT DOCUMENTS

| FR | 2282265 | 4/1976 |
| RU | 2038088 | 6/1995 |
| SU | 1 826 909 | 8/1990 |

OTHER PUBLICATIONS

Mashkovsky, M.D., Medicinal Preparations (a manual in pharmacotherapy for practitioners), 10$^{th}$ Edition, Moscow, Medicina Publishers, 1986, pp. 281–282.

Egorov, E.A., et al., "Clinical Studies of the Antioxidant Emosipine in Ocular Diseases," уДк 617.7–085.272.014.425–036.8. (1995).

Derwent Abstract 199612, Dagadova et al., 1990.*
Derwent Abstract 199501, Dagadova et al., 1990.*

* cited by examiner

*Primary Examiner*—Zohreh Fay
(74) *Attorney, Agent, or Firm*—Pennie & Edmonds LLP

(57) ABSTRACT

A pharmaceutical composition is provided which comprises an isotonic solution of an 0.02% mixture of di- and trisodim salts of echinochrome (Histochrome). It meets the requirements that apply to injectable formulations. Histochrome administration to human patients normalizes metabolic processes and eliminates inflammation in the retina, vascular membrane and cornea of the eye, improves trophic functions, reduces edema and accelerates epithelization.

12 Claims, No Drawings

HISTOCHROME AND ITS THERAPEUTIC USE IN OPHTHALMOLOGY

This application is a continuation of the U.S. national stage designation of PCT application Ser. No. RU99/00248, filed Jul. 21, 1999, the entire contents of which are incorporated herein by reference.

FIELD OF THE INVENTION

The present invention relates to medicine and, more specifically, to a novel pharma-ceutical composition useful in the treatment of ophthalmic diseases.

BACKGROUND OF THE INVENTION

At present, the role of free-radical peroxidation in the development of various diseases of the retina, optic nerve and other structures of the eye is well appreciated. For this reason, antioxidants are used increasingly in the treatment of ocular diseases. These compounds are able to alleviate inflammatory resorptive phenomena, to accelerate epithelization of the cornea and to reduce the incidence of dangerous complications that may result in the death of the eye.

The synthetic antioxidant Emoxipin (2-ethyl-6-methyl-4-oxypyridine) is known by its ability to reduce the capillary permeability and to inhibit blood coagulation. Injection of a 1% solution of this compound facilitates the resorption of intraocular hemorrhages. Emoxipin is clinically used in the treatment of chemical and thermal burns of the eye and in the keratoplasty of burn-related leukomas. However, monitoring of the blood coagulation system is required in the course of Emoxipin therapy, since this compound is liable to cause reccurrent hemorrhages (Egorov E. A., Shvedova A. A., Obraztsova I. S. Results of a clinical study of the antioxidant Emoxipin in the treatment of eye diseases. Vestnik Oftalmologii, 1989, No. 5, pp. 52-55, in Russian).

Also known in the prior art is the use of an 0.5% echinochrome solution in the treatment of eye burns (RU 2 038 088). Subconjunctival and parabulbar administration of an 0.5%-echinochrome solution to rabbits showed that it is able to facilitate epithelization of the cornea at early stages of the treatment of eye burns and to alleviate inflammatory processes in the eye.

However, clinical studies using an 0.5% echinochrome solution showed that patients experienced acute pain at the time of administration.

DISCLOSURE OF THE INVENTION

The objective of the present invention is to provide a novel and highly effective pharma-ceutical composition for the treatment of ophthalmic diseases, which would also meet the requirements that apply to injectable formulations.

The pharmaceutical composition of the present invention is based on echinochrome and has been specifically developed for the treatment of ophthalmic diseases. The composition of the present invention contains an 0.02% isotonic solution of di- and trisodium salts of echinochrome. The inventors established appropriate conditions under which a chemical interaction between the salt of a weak acid (sodium carbonate) and an organic compound (echinochrome) produces water-soluble sodium derivatives of echinochrome, in which 2 to 3 sodium ions are present per molecule of echinochrome.

Echinochrome, or 2,3,5,6,8-pentahydroxy-7-ethyl-1,4-naphthoquinone, is produced from a natural source (sea urchins, Latin echini), or by chemical synthesis.

The novel pharmaceutical composition Histochrome (trade mark) represents an isotonic solution for injections, containing a mixture of di- and trisodium salts of echinochrome in an amount of 0.018 to 0.022% in an 0.9% sodium chloride solution.

The solution thus prepared is sterilized by filtration through membrane filters and poured into 1 ml ampoules under aseptic conditions in an inert atmosphere. The ready-to-use composition is packaged in batches of 5-10 ampoules into boxes lined with PVC and aluminum foil. The boxes are placed into packs and 10-60 packs are placed into cardboard boxes and labeled in accordance with the requirements. The composition is stored protected from light at a temperature not exceeding 25° C. It has a shelf life of 2 years.

The composition is a yellow-brown transparent liquid.

The content of echinochrome, which is formed when Histochrome is acidified with hydrochloric acid, is determined spectrophotometrically. The optical density of a sample of the composition in acidified alcohol is compared with the optical density of a standard solution with a known concentration of echinochrome prepared under identical conditions.

The active ingredient is identified by its spectrum in acidified ethanol, which in the range of 250 to 600 nm has two absorption maxima ($342\pm2$ nm and $468\pm2$ nm) and two absorption minima ($295\pm2$ nm and $394\pm2$ nm).

The isotonocity of the sample is checked by mercurometric titration of sodium chloride using diphenilcarbazone as an indicator. The content of sodium chloride in the sample is in the range of 0.87% to 0.93%, and the pH is 6.5 to 7.5.

The composition is sterile. Histochrome itself has a marked antimicrobial activity.

The composition of the present invention is effective in the treatment of inflammatory diseases of the cornea, vascular membrane and retina of the eye; in the treatment of trophic disorders and resorption of hemorrhages in the vitreous body and retina. Histochrome may be used in proliferative processes, to reduce edema and to improve epithelization, as well as in the treatment of concussions and penetrating wounds of the eye. The composition has well-pronounced retinoprotective properties, improves characteristics of degenerative processes in the retina and the optic nerve. Histochrome was also found to act as an anticataractic agent.

PREFERRED EMBODIMENT OF THE INVENTION

The composition of the present invention was clinically studied in humans. Histochrome was used to treat hyphemia. Hyphemia is a complication that occurs after surgical removal of a cataract in the presence of severe myopia, hypertension-based glaucoma stage 2 or 3, amotio retinae after repeated surgery. Hyphemia cases covered the range from 1 mm up to a complete filling of the entire anterior eye chamber with blood. Hyphemia was resolved in 12 out of 14 patients treated. The following pattern of the resorption of hemorrhages was observed by biomicroscopy: the first 2-3 injections of Histochrome were followed by loosening and lique-faction of the blood clot, but its volume was not significantly reduced under these conditions. During the subsequent 2-3 days a rapid resorption occurred and no traces of hemorrhage remained on day 5 and 6 in the anterior chamber. In this group of patients the acuity of vision increased from 0.05 to 0.4 in 8 cases (57.1%).

Clinical effects of Histochrome in patients with hemophthalmia were dependent on the localization and extent of a hemorrhage, accompanying pathology, and time to onset of therapy. Minor hemorrhages in the anterior compatrment of the vitreous body were resolved rapidly and without affecting its structure in any significant manner. The resorption of hemorrhages in hemophthalmia patients was 3-4 days faster in the Histochrome-treated group than in the control group, and no visible damage of the vitreous body was apparent. Considering the fact that blood decomposition products produce toxic effects on the retina thereby disturbing its functions, a rapid resorption of hemorrhages provides favourable conditions for an active restoration of the functional capacity of the retina.

Histochrome administration parabulbarly (5-6 injections) to patients with diabetic retinopathy resulted in a reduction of edema zones and resorption of hemorrhages in the retina (a decrease both in terms of surface area and height). The acuity of vision increased from 0.03 to 0.6. As early as after 2-3 injections the patients reported an improvement of their vision. Electrophysical studies revealed an improved functioning of the optic nerve and the retina. Histochrome improved metabolical processes in the optic nerve and the retina and produced a protective effect. Considering the fact that diabetes-related ocular diseases tend to progress further, even a slight improvement of vision is regarded as a positive factor. Moreover, the resorption of subretinal hemorrhages and reduced edemas in the retina provide good conditions for carrying out an effective and high-quality laser-induced coagulation of the retina.

A positive therapeutic effect of Histochrome was also oserved in patients with keratitis. They were given an 0.02% Histochrome solution in the form of daily instillations 4 to 5 times a day. From the very first days of the histochrome therapy reductions in the pericorneal infections in the conjunctiva and in the corneal edema were observed. Epithelization of the cornea occurred 3-4 days earlier that in the case of treatment with conventional therapeutic compositions.

Clinical trials of subconjunctival and parabulbar administration of Histochrome in a dose of 0.5 ml (0.02%) showed no side effects, not a single case was reported. No contraindications against the use of Histochrome were found.

INDUSTRIAL APPLICABILITY

In ophthalmological practice the composition of the present invention is prescribed for the treatment of diseases associated with disturbances in the metabolic and inflammatory processes in the retina, vascular membrane and cornea of the eye, for improving trophic functions, for reducing edema and for accelerating epithelization. An 0.02% histochrome solution is administered in the form of subconjunctival and parabulbar injections in doses of 0.3-0.5 ml. Injections are made daily or every other day, depending on indications. For the treatment of corneal diseases the Histochrome solution from ampoules is used in the form of instillations, 2 drops, 4-5 times a day.

What is claimed is:

1. A pharmaceutical composition for the treatment of opthalmic diseases comprising an isotonic solution of 0.018 to 0.022 percent of di- and tri-sodium salts of 2,3, 5,6,8-pentahydroxy-7-ethyl-1,4-napthoquinone in a 0.9 percent sodium chloride solution.

2. A method of treating ophthalmic diseases in a subject comprising administering to said subject a therapeutically effective amount of a composition comprising an isotonic solution of 0.018 to 0.022 percent of di- and tri-sodium salts of 3,5,6,8-pentahydroxy-7-ethyl-1,4-mapthoquinone in a 0.9 percent sodium chloride solution.

3. The method of claim 2, wherein the composition is administered as 5–6 injections over the course of a day.

4. The method of claim 2, wherein the composition is administered as 2 drops to 4 to 5 times a day.

5. The method of claim 3, wherein the composition is administered by injection in an amount of 0.3 to 0.5 mL.

6. The method of claim 2, wherein the ophthalmic diseases is a diseases associated with a metabolic and inflammatory process of the retina, vascular membrane, and cornea of the eye.

7. The method of claim 2, wherein the ophthalmic disease is hyphemia, hemophthalmia, diabetic retinopathy, or, keratitis.

8. The method of claim 2, wherein the composition is administered as 2 drops between 4 and 5 times a day.

9. A method for preparing a pharmaceutical composition for the treatment of opthalmic diseases comprising an isotonic solution of 0.018 to 0.022 percent di- and tri-sodium salts of 2,3,5,6,8-pentahydroxy-7-ethyl-1,4-napthoquinone in a 0.9 percent sodium chloride solution comprising:

dissolving di- and tri-sodium salts thereof 2,3,5,6,8-pentahydroxy-7-ethyl-1,4-napthoquinone in a 0.9 percent sodium chloride solution to provide a solution of the di- and tri-sodium salts of 2,3,5,6,8-pentahydroxy-7-ethyl-1,4-napthoquinone in a 0.9 percent sodium chloride;

sterile filtering the solution of di-and tri-sodium salts of 2,3,5,6,8-pentahydroxy-7-ethyl-1,4-napthoquinone in a 0.9 percent sodium chloride through a membrane filter to provide a sterile solution; and placing the sterile solution into an ampule.

10. The pharmaceutical composition of claim 1, wherein the composition is sterile.

11. The pharmaceutical composition of claim 1, wherein the composition has a pH value of from 6.5 to 7.5.

12. The method of claim 2, wherein the opthalmic disease is an inflammatory disease of the cornea, vascular membrane, or retina; a trophic disorder; or a hemorrhage in the vitreous body or retina.

* * * * *

UNITED STATES PATENT AND TRADEMARK OFFICE
CERTIFICATE OF CORRECTION

PATENT NO. : 6,384,084 B2
DATED : May 7, 2002
INVENTOR(S) : Elyakov et al.

It is certified that error appears in the above-identified patent and that said Letters Patent is hereby corrected as shown below:

<u>Column 4,</u>
Line 6, replace "2,3, 5,6,8" with -- 2,3,5,6,8 --.
Line 13, replace "3,5,6,8-pentahydroxy-7-ethyl-1,4-mapthoquinone" with
-- 2,3,5,6,8-pentahydorxy-7-ethyl-napthoquinone --.
Lines 20 and 21, replace "ophthalmic diseases is a diseases" with -- ophthalmic disease is a disease --.
Line 34, replace "thereof" with -- of --.

Signed and Sealed this

Tenth Day of September, 2002

*Attest:*

JAMES E. ROGAN
*Attesting Officer*  *Director of the United States Patent and Trademark Office*